United States Patent [19]

Prusak et al.

[11] Patent Number: 4,503,806
[45] Date of Patent: Mar. 12, 1985

[54] LUBRICANT DETECTOR AND MEASURING DEVICE

[75] Inventors: John J. Prusak, Pike Township, Marion County, Ind.; Brian E. Lock, Princeton Borough, N.J.; Joseph H. Thorn, Indianapolis, Ind.

[73] Assignee: RCA Corporation, New York, N.Y.

[21] Appl. No.: 576,716

[22] Filed: Feb. 3, 1984

[51] Int. Cl.³ .................................... B05B 12/08
[52] U.S. Cl. ........................ 118/712; 118/689; 118/690; 118/300; 118/312; 427/8; 427/421; 239/74; 184/6.4; 184/6.26
[58] Field of Search ............... 118/712, 689, 690, 300, 118/326, DIG. 7; 427/8, 421, 424; 184/6.26, 6.4; 239/71, 74; 73/23, 28, 29

[56] References Cited

U.S. PATENT DOCUMENTS

| 3,612,859 | 10/1971 | Schumacher | 118/689 |
| 3,671,128 | 6/1972 | Radke et al. | 73/28 |
| 4,266,504 | 5/1981 | Roesner | 118/712 |
| 4,309,456 | 1/1982 | Lock | 427/209 |

Primary Examiner—Shrive P. Beck
Attorney, Agent, or Firm—Birgit E. Morris; Donald S. Cohen

[57] ABSTRACT

A detector and measuring device for determining the presence and number of lubricant particles in a flow of air directed onto the surface of a disc to coat the disc with a thin layer of the lubricant. The detector includes means for removing a portion of the air containing the lubricant particles from the coating chamber, means for diluting the air containing the lubricant particles with additional clean air and means for passing diluted air through a particle counter which detects and counts the particles of lubricant.

4 Claims, 1 Drawing Figure

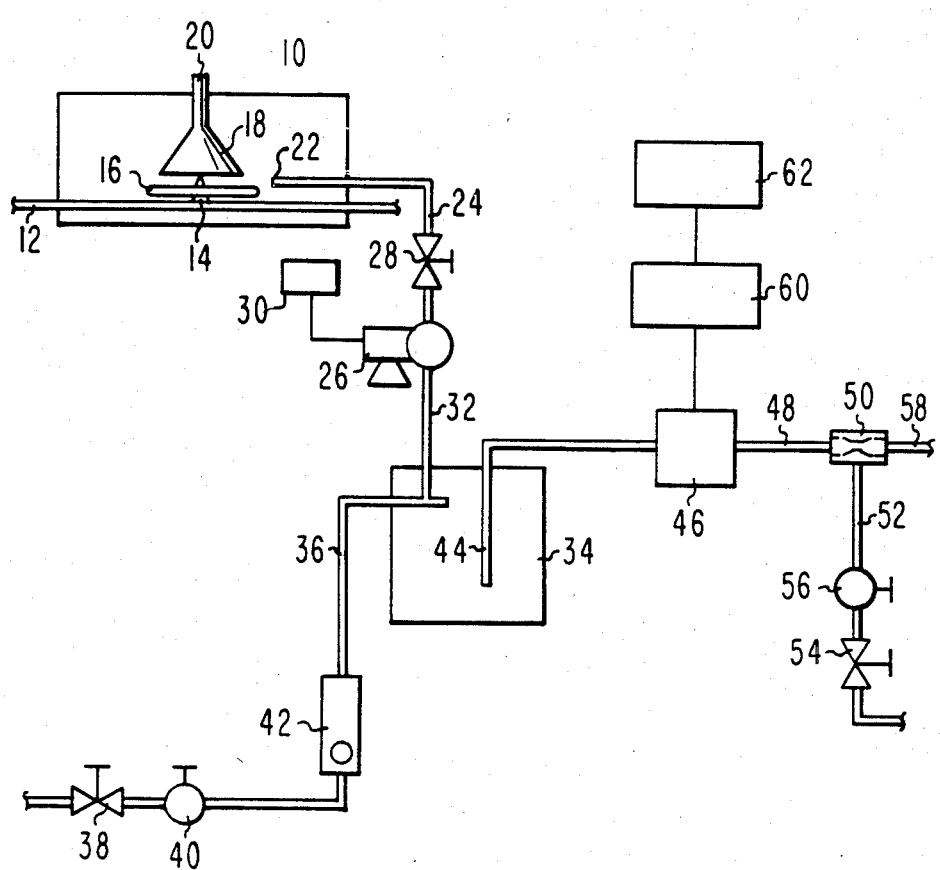

LUBRICANT DETECTOR AND MEASURING DEVICE

The present invention relates to a lubricant detector and measuring device and, more particularly, to a device for determining the number of lubricant particles present in an apparatus for applying a film of lubricant to the surfaces of an information recorded disc, such as a video disc.

BACKGROUND OF THE INVENTION

There has been recently developed a high density information recorded disc, i.e. a video disc, in which the recorded information is in the form of a surface relief pattern formed along a spiral path or track in a major surface of the disc. For a capacitive electronic disc (CED) the surface of the disc is conductive. The disc is played with a conductive stylus which follows the track on the surface of the disc. In order to reduce frictional forces and reduce wear of the stylus and/or disc, the disc is preferably coated with a thin layer, about 200 Angstroms thick, of a lubricant.

U.S. Pat. No. 4,309,456 to Brian E. Lock, issued Jan. 5, 1982, entitled "Method and Apparatus For Coating Recorded Discs With A Lubricant" describes a method and apparatus for applying a thin coating of lubricant to a disc. The apparatus described in this patent includes an atomizer for forming fine particles of the lubricant and a flow of air for carrying the lubricant particles from the atomizer to nozzles in a coating chamber. The disc passes through the chamber and across the nozzles which direct the flow of lubricant particles onto the major surfaces of the disc. Although this patent shows the disc passing through the coating chamber in an upright position with the nozzles directing the flow of the lubricant particles in a horizontal direction against the major surface of the disc, the disc can pass through the coating chamber horizontally with one major surface facing upwardly and a nozzle directing the flow of the lubricant particles vertically downwardly onto the surface of the disc. The disc would then be turned over to coat the other surface.

In order to insure that the desired amount of lubricant is being coated on the disc, it is desirable to determine the presence and quantity of the lubricant particles delivered by the nozzle on a continuous basis. Also, this determination must be made at the nozzle end of the coating apparatus rather than at the atomizer where the lubricant particles are generated, because there could be some problem in the line between the atomizer and the nozzle which would affect the flow of the lubricant particles to the nozzle.

SUMMARY OF THE INVENTION

An apparatus for coating the surface of a disc with a film of a lubricant includes a housing, a nozzle in the housing for directing a flow of air containing lubricant particles onto the surface of the disc and means for providing a flow of air containing lubricant particles to the nozzle. The apparatus also includes means for removing from the chamber a portion of the air containing lubricant particles emitted from the nozzle and means for counting the number of lubricant particles in the removed air.

BRIEF DESCRIPTION OF THE DRAWING

The drawing is a schematic of a disc coating apparatus which includes a form of a system incorporating the present invention for detecting and measuring the amount of lubricant being applied to the disc.

DETAILED DESCRIPTION OF PREFERRED EMBODIMENT

Referring to the drawing, a coating apparatus which with the detector device of the present invention is used includes a coating chamber 10 having a continuous conveyor 12, such as a conveyor belt, extending therethrough along a horizontal path. The conveyor belt 12 includes a support 14 on which is mounted in a horizontal plane a disc 16 to be coated. The disc 16 is carried through the coating chamber 10 with one of its major surfaces facing vertically upwardly. A nozzle 18 is mounted in the chamber 10 with its exit end being directly over the path of travel of the major surface of the disc 16. The nozzle 18 is connected by a pipe 20 to a source of a flow of air containing particles of a lubricant. The source of the air carrying the lubricant particles may be an atomizer of the type shown and described in the Lock U.S. Pat. No. 4,309,456, which is incorporated herein by reference. Thus, the nozzle 18 is positioned to direct the flow of the air carrying the lubricant particles vertically downwardly against the surface of the disc 16.

A tube 22 extends from within the chamber 10 adjacent the outlet end of the nozzle 18 and is connected to a pipe 24 which extends to a pump 26. The pump 26 is of the type which will withdraw material from within the chamber 10 through the tube 22 and pipe 24. A valve 28 is provided in the pipe 24 to control the flow of material to the pump 26. The pump 26 is also provided with a controller 30 for controlling the speed of the pump. A pipe 32 extends from the outlet of the pump 26 to a chamber 34. A pipe 36 extends between the chamber 34 and a source of clean air, not shown. Along the pipe 36 is a control valve 38, a pressure regulator 40 and a flow meter 42.

An outlet pipe 44 extends from within the chamber 34 to a particle counter 46. The particle counter 46 may be of any type which is capable of counting particles of a liquid within a flow of air, such as a RAM-1 Real Time Aerosol Monitor made by GCA Co. The particle counter 46 is connected by a pipe 48 to an aspirator 50. The aspirator 50 is fed with a flow of clean air through a pipe 52 from a source not shown. The pipe 52 includes a control valve 54 and a pressure regulator 56. An exhaust pipe 58 extends from the outlet end of the aspirator 50. The particle counter 46 is connected to a readout 60 which provides a visual readout of the particle counter and to a strip chart 62 which provides a permanent record of the readout.

In the operation of the coating apparatus a flow of air filled with particles of the lubricant is directed by the nozzle 18 onto the surface of the disc 16. A portion of this flow of air filled with the lubricant particles is continuously withdrawn from the chamber 10 through the tube 22 and pipe 24 by the pump 26. This portion of the air filled with the lubricant particles is delivered by the pump 26 through the pipe 32 to the chamber 34. Additional clean air is delivered into the chamber 34 through the pipe 36 to dilute the air filled with the lubricant. The air filled with the lubricant is preferably diluted to about 4000 parts of air to one part of lubricant.

Air is fed through the pipe 52 to the aspirator 50. This generates a vacuum which pulls some of the diluted air, lubricant particle mixture from the chamber 34 up through the pipe 44 and through the particle counter 46 where the particles of the lubricant in the air are counted. The results of the count are shown on the readout 60 and recorded on the strip chart 62.

Thus, the readout 60 and the strip chart 62 provide a continuous indication of whether lubricant particles are being delivered to the disc 16 and also the number of lubricant particles in the flow of air to the disc 16. The readout 60 and/or strip chart 62 can be connected to suitable switches which will stop the operation of the coating apparatus in the event that the count of the lubricant particles becomes too low and/or set off an alarm. Thus, the detector device can be used to control the operation of the coating apparatus. By diluting the air filled with the lubricant particles with additional air prior to passing the air through the particle counter 46, there is provided a higher sensitivity in the counting of the lubricant particles.

We claim:

1. In an apparatus for coating the surface of an article with a film of a liquid material which includes a chamber, a nozzle in said chamber for directing a flow of air containing particles of said liquid material onto the surface of the article and means for providing a flow of air containing said particles to the nozzle, the improvement comprising:
    a tube in said housing having one end adjacent said nozzle,
    a pump having its inlet end connected to the other end of said tube for removing from the housing a portion of the air containing the particles,
    means for diluting the air containing the particles with additional air, said means being connected to the outlet end of the pump, and
    means for counting the number of particles in the diluted mixture of air and particles.

2. An apparatus in accordance with claim 1 in which the means for diluting the air containing the particles includes a chamber to which the outlet of the pump is connected and means for delivering clean air to the dilution chamber.

3. Apparatus in accordance with claim 2 including means for withdrawing the diluted air containing the particles from the dilution chamber and passing it through a particle counter.

4. Apparatus in accordance with claim 3 in which the particle counter is connected to the dilution chamber and an aspirator is connected to the particle counter to draw the diluted air from the dilution chamber through